United States Patent
Vanderveen

(10) Patent No.: US 7,356,382 B2
(45) Date of Patent: *Apr. 8, 2008

(54) SYSTEM AND METHOD FOR VERIFYING CONNECTION OF CORRECT FLUID SUPPLY TO AN INFUSION PUMP

(75) Inventor: Timothy W. Vanderveen, Poway, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/503,799

(22) Filed: Aug. 14, 2006

(65) Prior Publication Data

US 2006/0276936 A1 Dec. 7, 2006

Related U.S. Application Data

(63) Continuation of application No. 10/714,827, filed on Nov. 14, 2003, now Pat. No. 7,092,796.

(51) Int. Cl.
*G05D 11/00* (2006.01)
(52) U.S. Cl. .................. 700/282; 700/281; 604/67; 604/131
(58) Field of Classification Search .............. 700/282; 604/65–67, 80, 81, 410; 210/85
See application file for complete search history.

(56) References Cited

U.S. PATENT DOCUMENTS

| 4,705,506 A | 11/1987 | Archibald et al. |
| 4,714,463 A | 12/1987 | Archibald et al. |
| 4,795,429 A | 1/1989 | Feldstein |
| 5,116,203 A | 5/1992 | Natwick et al. |
| 5,213,483 A | 5/1993 | Flaherty et al. |
| 5,312,334 A | 5/1994 | Hara et al. |
| 5,378,231 A | 1/1995 | Johnson et al. |
| 5,522,798 A | 6/1996 | Johnson et al. |
| 5,527,289 A * | 6/1996 | Foster et al. ............ 604/151 |
| 5,547,470 A | 8/1996 | Johnson et al. |
| 5,695,473 A * | 12/1997 | Olsen ..................... 604/153 |
| 5,827,223 A | 10/1998 | Butterfield |

(Continued)

FOREIGN PATENT DOCUMENTS

WO   WO 03/059418 A1   7/2003

OTHER PUBLICATIONS

International Search Report, International Application No. PCT/US2004/037708, Jun. 10, 2005.

*Primary Examiner*—Alexander Kosowski
(74) *Attorney, Agent, or Firm*—McDermott Will & Emery

(57) ABSTRACT

A system and method for verifying that a particular fluid supply is connected to an infusion pump or pump channel. An upstream pressure sensor coupled to a fluid conduit associated with the fluid supply is used to provide pressure signals in response to pressure sensed in the conduit to a processor. In a connection verification mode, the processor is configured to receive the pressure signals and delay the flow control device of the infusion pump from moving fluid through the conduit until the processor detects a pressure change in the conduit indicated by the pressure signals to thereby verify that the particular fluid supply is connected to the infusion pump.

26 Claims, 5 Drawing Sheets

U.S. PATENT DOCUMENTS

| | | |
|---|---|---|
| 5,951,510 A | 9/1999 | Barak |
| 5,974,708 A | 11/1999 | Webb et al. |
| RE36,871 E | 9/2000 | Epstein et al. |
| 6,325,422 B1 | 12/2001 | Verkaart et al. |
| 6,423,029 B1 * | 7/2002 | Elsberry ............ 604/65 |
| 6,458,104 B2 | 10/2002 | Gautsche |
| 6,497,680 B1 | 12/2002 | Holst et al. |
| 6,511,456 B1 | 1/2003 | Salinas et al. |
| 6,613,012 B2 | 9/2003 | Kraushaar |
| 6,757,630 B2 | 6/2004 | McClendon et al. |
| 2002/0183693 A1 | 12/2002 | Peterson et al. |
| 2003/0004469 A1 | 1/2003 | Kraushaar |
| 2004/0193328 A1 | 9/2004 | Zaitsu et al. |

\* cited by examiner

SYSTEM AND METHOD FOR VERIFYING CONNECTION OF CORRECT FLUID SUPPLY TO AN INFUSION PUMP

CROSS-REFERENCES TO RELATED APPLICATIONS

This is a continuation of application Ser. No. 10/714,827, filed on Nov. 14, 2003 now U.S. Pat. No. 7,092,796.

BACKGROUND OF THE INVENTION

The invention is generally related to fluid infusion, and more particularly, to a fluid infusion system and method that verifies that the correct fluid supply is connected to the correct infusion pump.

Physicians and other medical personnel apply intravenous (IV) infusion therapy to treat various medical complications in patients. IV infusion therapy typically involves infusing medical fluids, such as drugs or nutrients, from a fluid supply, such as a bag, bottle or other container, through the tube of a fluid administration set to a cannula inserted into a patient's blood vessel. In a typical facility, a physician enters an order for medication for a particular patient. This order may be handled either as a simple prescription slip, or it may be entered into an automated system, such as a physician order entry ("POE") system. The prescription slip or the electronic prescription from the POE system is routed to the pharmacy, where the order is filled. Typically, the prescribed medication is prepared by a pharmacist and added to a bag or bottle at a pharmacy. A pharmacist also typically identifies the contents of the bag and the patient for whom the bag is intended with a paper label that is attached to the bag and in some cases by other means, such as a bar code or magnetic device, or by use of a radio frequency (RF) signal interactive device such as an RFID tag, as examples. The prepared medication is then delivered to a nurse's station for subsequent administration to the patient.

For safety reasons and in order to achieve optimal results, the medical fluid is often administered in accurate amounts as prescribed by the doctor and in a controlled fashion by using an infusion pump. Infusion pumps operate by displacing the fluid from a fluid administration set to force fluid from the fluid supply through the tube and into the patient. The infusion pump is programmed by an operator such as a nurse or other medical personnel, with operating parameters to achieve the administration of the drug as prescribed by the physician. Such operating, or pumping, parameters are drug and patient specific. That is, the pumping parameters are selected based on the particular drug prescribed and the specific patient for whom they are intended. It is the nurse's responsibility to match the prescribed drug with the correct patient and with the properly programmed pump.

Hospitals and other institutions continually strive to provide quality patent care. Medical errors, such as when a patient receives the wrong drug or receives the correct drug at the wrong time or in the wrong dosage, are significant problems for all health care facilities. In the administration of medication, focus is typically directed to the following five "rights" or factors: the right patient, the right drug, the right route, the right amount, and the right time. The nurse aims to ensure that these "rights" are accomplished. Systems and methods seeking to reduce medical errors should also take these five rights into consideration.

Medical infusion pumps have advanced greatly over the years and permit more precise infusion control resulting in much better treatment for patients. Doctors are more assured that the doses and infusion rates that they prescribe for their patients can be delivered to the patients accurately by infusion pumps. However, there remains a continuing concern that the right drug is matched to the right pump.

In some cases, a single patient may be prescribed multiple simultaneous infusions for different drugs, sometimes four or more, which requires multiple infusion pumps that may all be programmed differently. In such cases, there will also be multiple administration sets each with its own fluid conduit to be connected with the patient. Where there are multiple infusion conduits present, there is a concern that a fluid conduit may be mounted to the wrong infusion pump and the drug delivered under incorrect pumping parameters. As an example, where multiple infusion pumps are located side by side, there is a concern that a fluid infusion line may be installed in the wrong pump channel. Where a more dense infusion pump environment exists, it is important to be sure that the correct medical fluid conduits are being mounted to the correct pump or "channel." The four fluid sources for all four pump channels may be suspended immediately above all four pump channels and the conduits of the four administration sets may become intertwined, thus making it more difficult to select the correct tube for the particular channel of the pump.

Prior attempts have been made to assure that the right drug is administered to the right patient through the right pump. In one example, a bar code label identifying the drug and patient is applied to the bag at the pharmacy. After an operator such as a nurse manually programs the pump, a bar code scanner connected to the pump is used to read the bar code label on the bag to verify that it identifies the same medication as that programmed into the pump. In another example, U.S. Pat. No. 5,078,683 to Sancoff et al. discloses a bar code label applied to the bag that is read with a bar code scanner to automatically program the pump, thus avoiding manual programming entirely.

Even though the foregoing have provided significant advances in the art to avoid medication errors and have reduced the likelihood of such medication errors, there still exists some risk that an incorrect bag may become mounted to a pump or pump channel. Stated differently, there still exists some risk that a bag may become connected to the wrong pump or pump channel. For example, the nurse could possibly scan the bar code label of the correct bag, but become distracted and mount the conduit of the administration set connected to the bag to the wrong pump channel. Even if the nurse does not become distracted, the various fluid conduits in a multiple fluid infusion may be difficult to distinguish from one another and tracing the fluid conduit associated with the right bag may become burdensome, especially where the fluid conduits have become tangled with each other. In such a case, the nurse may inadvertently choose the wrong fluid conduit to install in the pump even after identifying the correct fluid supply.

Hence, those skilled in the art have recognized that a need still exists for a system and method to more accurately ensure that the correct fluids are infused into the patient at the correct pumping parameters. Further, those skilled in the art have recognized a need for a system and method that can more reliably determine that the correct fluid source is connected to the correct infusion pump or pump channel so that the fluid is infused into the patient in accordance with the correct pumping parameters. The present invention fulfills these needs and others.

INVENTION SUMMARY

Briefly and in general terms, the present invention is directed to a system and method for verifying that an infusion pump is set up correctly for administering a fluid. Further, the invention is directed to verifying that the correct fluid supply is connected to a pump or pump channel.

In more detailed aspects, a system for verifying that a particular fluid supply is connected to a flow control device is provided, wherein the flow control device acts on a fluid conduit coupled to the fluid supply to move the fluid from the fluid supply through the conduit, the fluid supply and conduit forming an upstream fluid supply segment, the system comprising a pressure sensor assigned to the flow control device and coupled to the fluid conduit at a location between the fluid supply and the flow control device, the pressure sensor sensing pressure of the conduit and providing pressure signals in response to such sensed pressure, and a processor having a connection verification mode in which the processor is configured to provide a verification indication when the processor receives pressure signals indicative of an expected pressure change in the conduit to thereby verify that the particular fluid supply is connected to the flow control device.

In more detailed aspects, the processor is further configured to delay the flow control device from moving fluid through the conduit until the processor receives pressure signals indicative of an expected pressure change in the conduit to thereby verify that the particular fluid supply is connected to the flow control device. Also, the processor in the connection verification mode is configured to detect that the expected pressure change is at a second flow control device and indicate an identity of the second flow control device. In another aspect, the processor in the connection verification mode is further configured to prompt an operator to induce a pressure change in the fluid conduit, and monitor the pressure signals to detect the operator-induced pressure change.

In other aspects, the processor in the connection verification mode is further configured to monitor the pressure signals for a predetermined time period to detect the induced pressure change, and prompt the operator to confirm that a pressure change has been induced if the induced pressure change is not detected within the predetermined time period. The processor in the connection verification mode is further configured to provide an alert indication if the operator confirms that the pressure change has been induced but the processor has not detected a pressure change indicated by the pressure signals within the predetermined time period.

In further detailed aspects, the processor in the connection verification mode is configured to prompt the operator to squeeze the upstream fluid supply segment to induce the pressure change in the fluid conduit. In another aspect, the processor in the connection verification mode is configured to prompt the operator to change the height of the particular fluid supply to induce the pressure change in the fluid conduit. In yet a further aspect, the processor in the connection verification mode is configured to prompt the operator to tap the upstream fluid supply segment to induce the pressure change.

In other aspects in accordance with the invention, the pressure sensor is mounted to the flow control device and is located adjacent and upstream in relation to the flow control device. Further, the pressure sensor is located and configured such that when the fluid conduit is mounted at the flow control device, the fluid conduit also must be mounted in operable communication with the pressure sensor.

More aspects include that the processor comprises an override mode, the processor being configured such that when in the override mode, the processor does not run the verification mode. The system further comprises a memory connected with the processor, wherein the processor is further configured to store data in the memory indicating that the processor was configured in the override mode. Additionally, the processor is configured such that when in the override mode, the processor does not delay the flow control device from moving fluid through the conduit.

Yet another aspect includes a drug library in which is stored a data base of drugs, wherein the drug data base also includes instructions linked to selected drugs to instruct the processor to run the connection verification mode, and an input device coupled to the processor by which a selection of a drug from the drug data base is made, wherein the processor receives the drug selection from the input device, accesses the drug library, and is configured in the connection verification mode in the event that such an instruction is linked to the selected drug.

Also provided is a method for verifying that a particular fluid supply is connected to a flow control device, wherein the flow control device acts on a fluid conduit coupled to the fluid supply to move the fluid from the fluid supply through the fluid conduit, the fluid supply and fluid conduit forming an upstream fluid supply segment, the method comprising prompting an operator to induce a pressure change in the fluid conduit, sensing pressure in the fluid conduit upstream from the flow control device and generating pressure signals in response to the pressure sensed, processing the pressure signals to detect a pressure change in the fluid conduit in response to the step of prompting the operator to induce the pressure change, and indicating a connection verification that the fluid supply is connected to the flow control device when the induced pressure change is detected from processing the pressure signals.

Further method aspects include delaying the flow control device from moving fluid through the conduit until the pressure change in the fluid conduit is detected. Another aspect includes detecting the expected pressure change at a second flow control device, and indicating an identity of the second flow control device. Yet further aspects include prompting an operator to induce a pressure change in the fluid conduit, and monitoring the pressure signals to detect the operator-induced pressure change, and delaying the flow control device from moving fluid through the conduit until the operator-induced pressure change is detected. Also, monitoring the pressure signals for a predetermined time period to detect the induced pressure change, and prompting the operator to confirm that a pressure change has been induced if the induced pressure change is not detected within the predetermined time period. A further aspect comprises providing an alert indication if the operator confirms that the pressure change has been induced but the processor has not detected a pressure change indicated by the pressure signals within the predetermined time period.

In more detailed method aspects, the method comprises prompting the operator to squeeze the upstream fluid supply segment to induce the pressure change in the fluid conduit, change the height of the particular fluid supply to induce the pressure change in the fluid conduit, or tap the upstream fluid supply segment to induce the pressure change.

In yet other aspects, the method comprises selectively overriding the processing, indicating, and delaying steps, and storing an override in a memory for later analysis. Additional method aspects include storing a drug library comprising a data base of drugs, wherein the drug data base also includes instructions linked to selected drugs to run a connection verification method, and selecting a drug from the drug data base, accessing the drug library and performing the prompting, sensing, processing, and indicating steps in the event that such an instruction is linked to the selected drug.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 1:
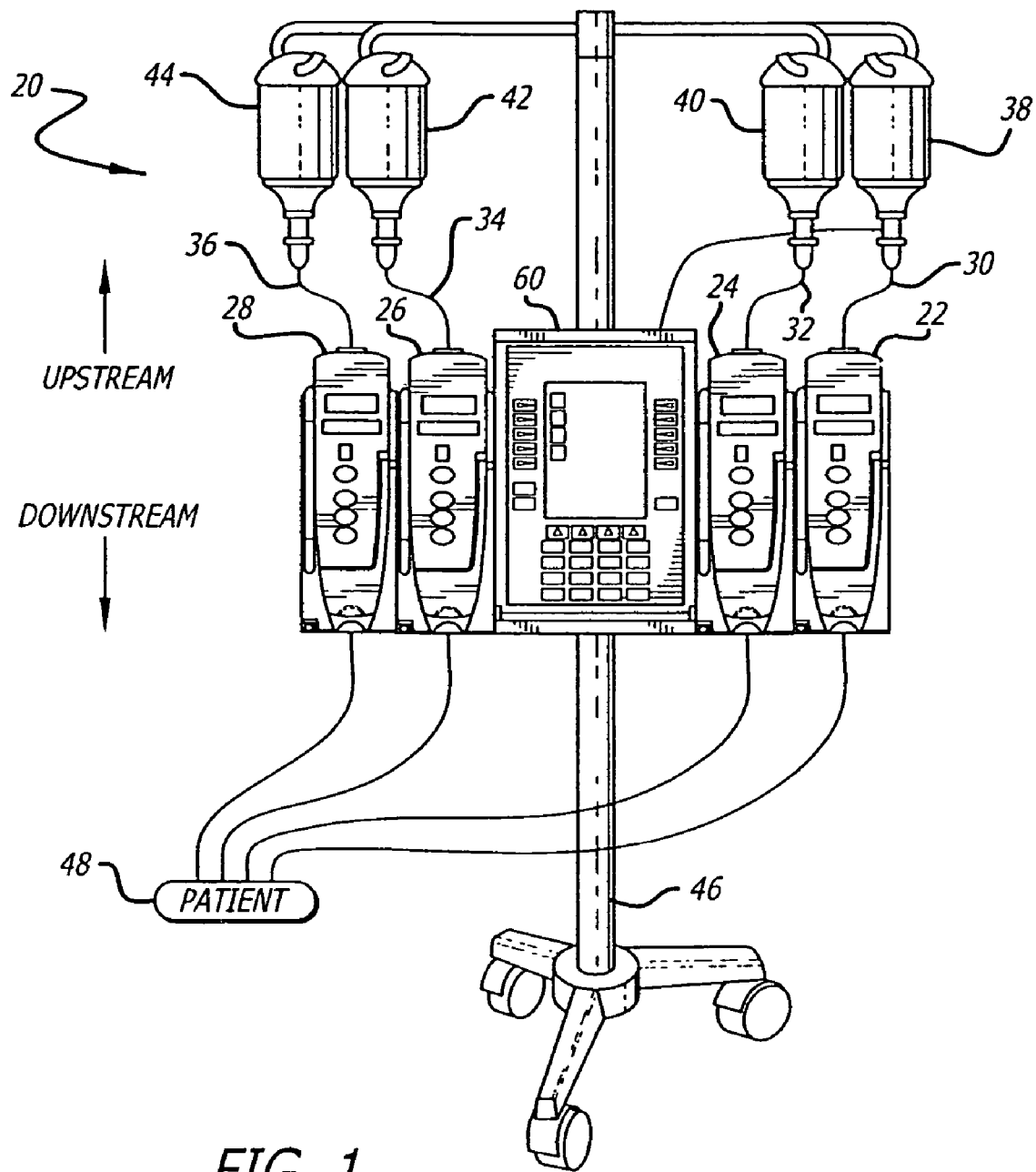
FIG. 1 is a front view of a patient care system having four fluid infusion pumps, each of which is connected to a respective fluid supply for pumping the contents of the fluid supply to a patient, the patient care system and fluid supplies being mounted on a common roller stand.

Referring now in more detail to the drawings in which like reference numerals refer to like or corresponding elements among the several views, there is shown in FIG. 1 a patient care system 20 having four infusion pumps 22, 24, 26, and 28 each of which is in operative engagement with a respective fluid administration set 30, 32, 34, and 36. Fluid supplies 38, 40, 42, and 44, which may take various forms but in this case are shown as bottles, are inverted and suspended above the pumps. Fluid supplies may also take the form of bags or other types of containers. Both the patient care system 20 and the fluid supplies 38, 40, 42, and 44 are mounted to a roller stand or IV pole 46.

Each administration set 30, 32, 34, and 36 is connected between a respective fluid supply 38, 40, 42, and 44 and the same patient 48 so that the patient may receive the fluids in all the fluid supplies. A separate infusion pump 22, 24, 26, and 28 is used to infuse each of the fluids of the fluid supplies into the patient. The infusion pumps are flow control devices that will act on the respective tube or fluid conduit of the fluid administration set to move the fluid from the fluid supply through the conduit to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other.

Typically, medical fluid administration sets have more parts than are shown in FIG. 1. Many have check valves, drip chambers, valved ports, connectors, and other devices well known to those skilled in the art. Except for FIG. 6 where a Y-site port is shown, these other devices have not been included in the drawings so as to preserve clarity of illustration.

In accordance with the background discussed above, it is desirable to verify the correct connection of each fluid supply 38, 40, 42, and 44 to the correct pump 22, 24, 26, and 28 prior to activating the pumping mechanism of a pump so that a fluid is not infused into the patient with incorrect pumping parameters.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater. There would be more of an opportunity for the tubes of the administration sets 30, 32, 34, and 36 to become intertwined with each other when all four are dangling from the bottles, which can cause confusion as to which tube should be in which infusion module. The opportunity for confusion increases as the number of tubes increases.

Figure 2:
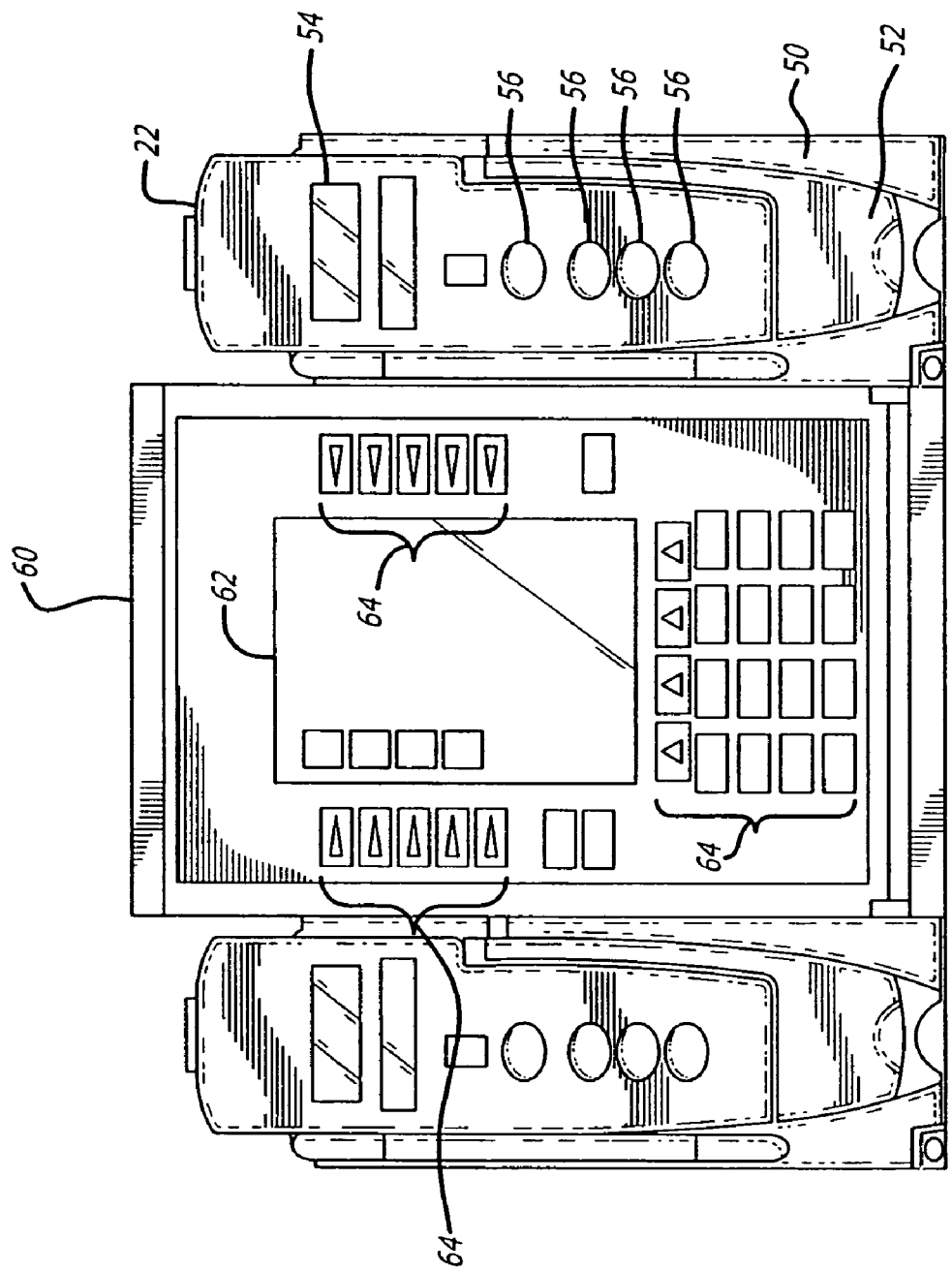
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 3. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker (not shown).

In the embodiment shown, a programming module 60 is attached to the left side of the infusion pump 24. Other devices or modules, including another infusion pump, may be attached to the right side of the infusion pump 24, as shown in FIG. 1. In such a system, each attached pump represents a pump channel of the overall patient care system 20. In one embodiment, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al. incorporated herein by reference in which the programming module is described as an advanced interface unit.

The programming module 60 includes a display 62 for visually communicating various information, such as the operating parameters of the pump 24 and alert indications and alarm messages. The programming module 60 may also include a speaker (shown in FIG. 4) to provide audible alarms. The programming module also has various input devices in this embodiment, including control keys 64 and a bar code scanner (not shown) for scanning information relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump. The communications system may take the form of a radio frequency ("RF") (radio frequency) system, an optical system such as infrared, a Blue Tooth system, or other wired or wireless system. The bar code scanner and communications system may alternatively be included integrally with the infusion pump 24, such as in cases where a programming module is not used, or in addition to one with the programming module. Further, information input devices need not be hard-wired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Figure 3:
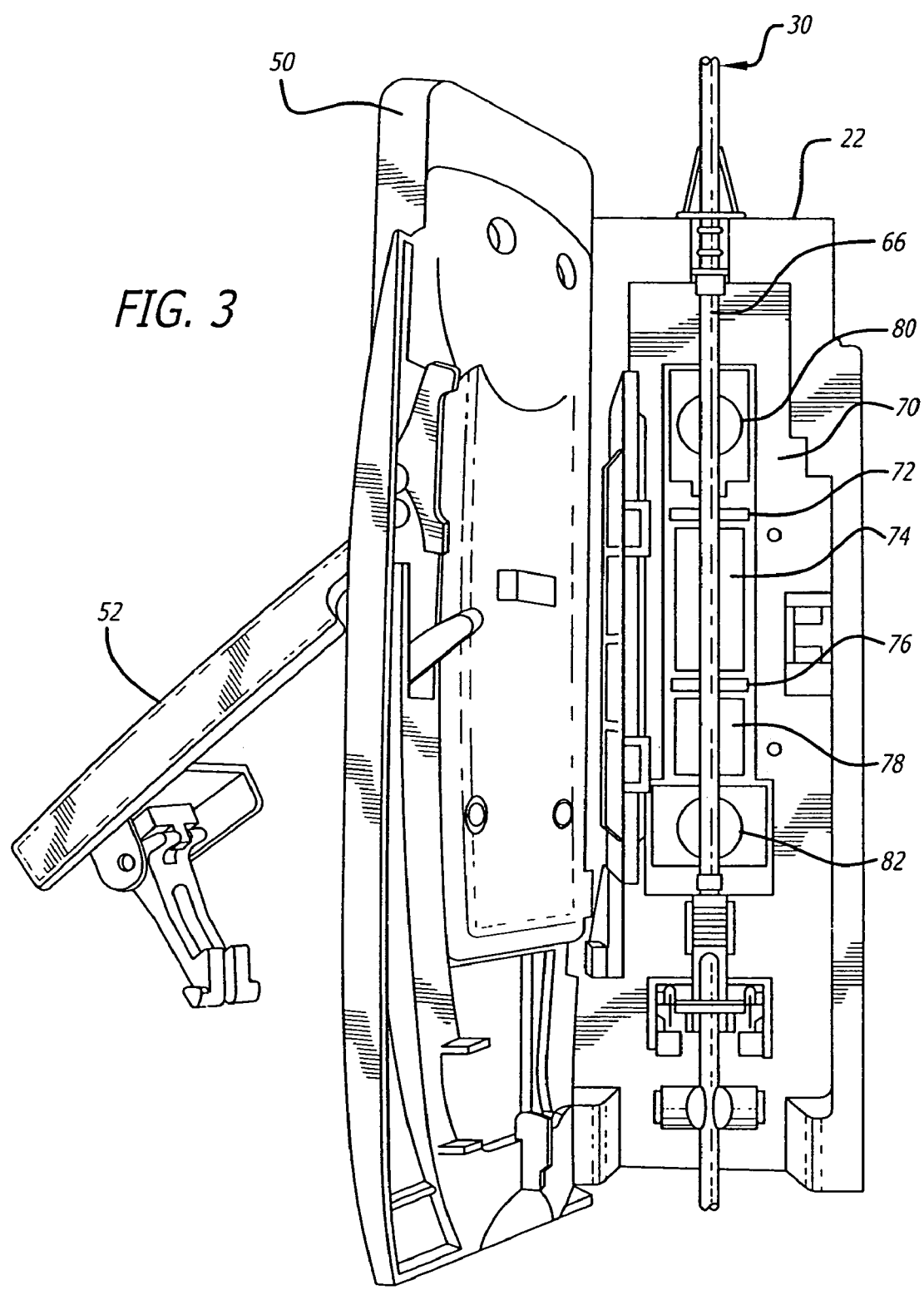
FIG. 3 is a perspective view of one of the fluid infusion pumps of FIGS. 1 and 2 with its front door in the open position showing an upstream pressure sensor used in accordance with aspects of the present invention, a downstream pressure sensor, a peristaltic four finger pump mechanism located between the sensors, and a fluid tube in operative engagement with the infusion pump.

Turning now to FIG. 3, an infusion pump 22 is shown in perspective view with the front door 50 open, showing the administration set 30 in operative engagement with the pump 22. The fluid administration set comprises a fluid conduit or tube 66, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit. In this case, the pumping mechanism is of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 3 further shows an upstream pressure sensor 80 used in accordance with aspects of the present invention. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient. A downstream pressure sensor 82 is also included in the pump 22 embodiment at a downstream location with respect to the pumping mechanism. A distinct advantage to having a pressure sensor located upstream of the pumping mechanism is that pressure in the upstream line can be continuously detected. As mentioned above, the pumping mechanism always provides an occlusion of the channel so that there is never an open fluid line from upstream of the pumping mechanism to downstream of the pumping mechanism. For pressure sensors located elsewhere, the pumping mechanism provides interference in determining upstream pressure.

Figure 4:
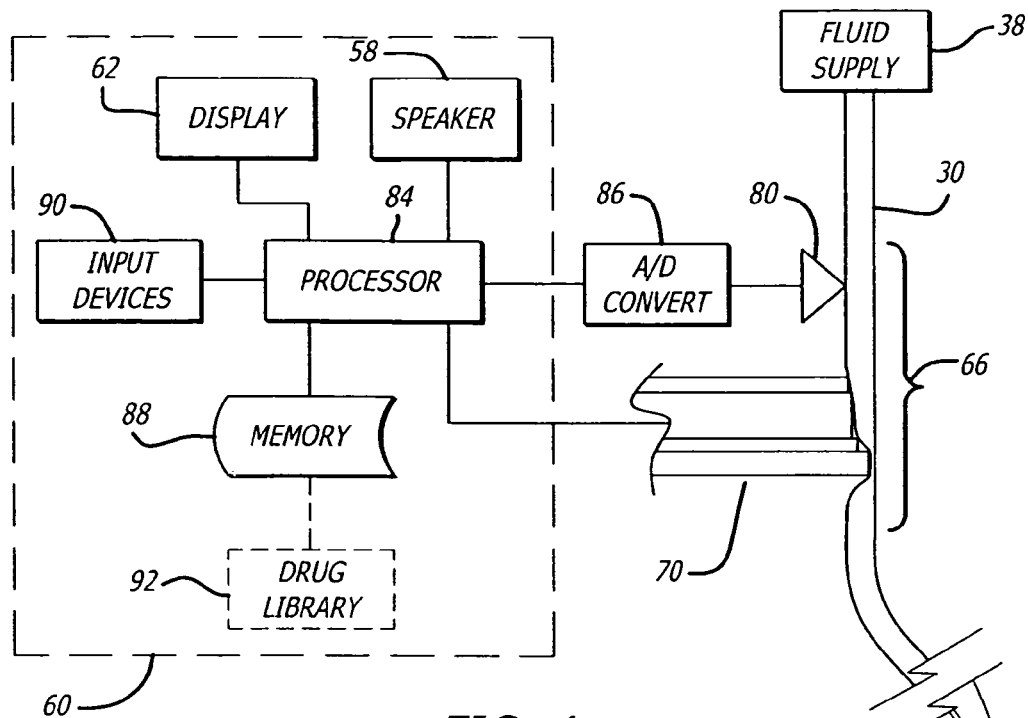
FIG. 4 is a block diagram showing components of one embodiment of a system incorporating aspects of the present invention, for verifying that the correct fluid source is connected to a pump.

Referring now to FIG. 4, the upstream pressure sensor 80 is shown coupled to the fluid conduit 66, as ordinarily occurs when the fluid conduit is loaded into the pump 22 and the pump door is closed (FIG. 1). The fluid conduit interconnects the fluid supply 38 with the patient 48 and provides a conduit for the fluid of the fluid supply to be infused into the patient. In one embodiment, the upstream pressure sensor is located and configured such that when the fluid conduit is mounted into the pumping mechanism or flow control device 70, it also must be mounted in operable communication with the upstream pressure sensor.

The upstream pressure sensor 80 may take many forms well known to those skilled in the art, including a piezoresistive device. Consequently, no further technical details concerning the mechanical formation of the sensor are presented herein. The sensor 80 provides pressure signals in response to pressure sensed in the conduit 30. Those pressure signals are analog in form and are converted to digital form by an analog-to-digital converter ("A/D") 86 integral with the sensor or by an A/D located elsewhere in the data stream. The digital pressure signals are supplied to a processor 84. In accordance with its programming, the processor is configured to receive the digital pressure signals and process them to detect pressure levels and pressure changes. In accordance with an aspect of the invention, the processor will be configured to detect a pressure change within a selected time period in order to determine if the correct fluid supply is connected with the pump and its associated pressure sensor. In the latter operation, the processor is referred to as running a connection verification mode.

Although FIG. 4 shows an embodiment of the present invention in which the processor 84 is connected with a single pump or flow control device 70, it should be understood that other embodiments may exist in which multiple pump channels associated with a multi-channel patient care system may be monitored by the same processor. In such an embodiment, the processor performs the same functions for each pump channel of the system. As an example, FIG. 1 shows a four pump system in which the four pumps 22, 24, 26, and 28 are connected to a common programming module 60 having an internal processor. The processor of the programming module 60 may perform the "connection verification mode" for all four pumps. Additionally, as is discussed in detail relevant to FIG. 7 below, a networked arrangement of separate, individual pumps may be provided wherein a processor of the network performs a like function as the programming module 60.

According to one aspect of the present invention, the processor 84 has a connection verification mode in which it delays the flow control device 70 from moving fluid through the conduit 66 to the patient 48 until the processor verifies that the correct conduit 30 is connected to the pump. This is done by the processor detecting a purposely induced pressure change in the upstream conduit. In determining if a pressure change has occurred, the processor may be configured to detect a pressure change that exceeds a minimum threshold in one embodiment. In another embodiment, the processor may be further configured to detect an appropriate pressure decay response subsequent to a detected pressure change.

Thresholds or other reference values for evaluating whether the induced pressure change has in fact occurred in the conduit connected with the pump may be stored in a memory 88 which the processor 84 can access. The programs of the processor, including the program supporting the connection verification mode, may be stored in the same memory 88, or in another memory (not shown). Use of memory to store programs and data is well known and no further details are provided here. Values and other programming may also be input into the memory using an input device 90, such as control keys, or may be preprogrammed.

In one embodiment of the connection verification mode, the processor 84 is configured to begin its connection verification mode when it senses the existence of a fluid conduit 66 connected to the pump. Sensing the existence of a fluid conduit connected to the pump may be performed in different ways, such by detecting a change in the pressure signals from either the upstream or downstream pressure sensors, or by other means. Once the processor senses that the door 50 of the pump has been closed and the door handle 52 locked, the processor will then await the programming of the pump for operating parameters, such as flow rate, an identification of the drug being infused, and possibly other parameters. The latter manual programming step may not be necessary if the pump has been automatically programmed, such as by use of a bar code reader that was used to input pump operating parameters from a bar code label mounted to the fluid supply.

Once the processor 84 determines that the pump 70 has been loaded with a conduit 30 and the pump has been programmed for operation, the processor will then request the operator of the pump to induce a pressure change in the conduit that should be connected to the pump. The operator may induce a pressure change by squeezing the bag 38 to which the conduit is connected for example, or by raising or lowering the bag or bottle thus changing the head pressure. In an alternative embodiment, the processor may suggest such ways to induce the required pressure change through a visual text or graphics indication on the display 62 of the programming module 60. Because the upstream pressure sensor 80 is located upstream of the pumping mechanism 70, it can continually monitor the pressure existing in the upstream portion of the conduit and can detect induced pressure changes. The processor thus controls the upstream pressure sensor to the "on" mode and continually monitors the pressure signals it provides. If the operator squeezes the correct bag, i.e. the one connected to the conduit mounted to the pump, an increase in pressure in the conduit will be sensed by the upstream sensor, and by the processor, and the correct fluid supply for the pump will have been verified.

Once the processor has instructed the operator to induce the pressure change, the processor will then wait for a predetermined period of time within which it expects to receive pressure signals indicating that the requested pressure change has been induced. During the predetermined period of time during which the processor is waiting to receive the induced pressure change, the processor inhibits or delays the flow control device 70 from moving fluid through the conduit 66. The predetermined time period may be set at fifteen seconds for example, or a different time period. During the time period, the processor may display an appropriate indication such as "WAITING FOR OPERATOR-INDUCED PRESSURE CHANGE" or "SQUEEZE DRUG CONTAINER TO VERIFY CORRECT SET LOADING" or other message, so the operator can immediately see what mode the processor and pump are in.

In yet other aspects, a processor that monitors multiple pumping channels, such as in the arrangement of the ALARIS MEDLEY® system, may be programmed to look for a pressure change in any of the channels when it prompts the operator to induce a pressure change in one channel. By this technique, the processor can then indicate to the operator in which channel the pressure change was actually detected. If the pressure change occurred in a channel other than the channel in which it was expected, the processor may indicate a misloading of the channel, but time will be conserved in that the processor may also indicate to the operator through a front panel display or through other means which channel in fact has the desired conduit. The operator can then quickly locate that conduit and place it in the correct channel.

If during the predetermined period of time within which the induced pressure change should occur no pressure change is received by the processor from the pump, the processor will then query the operator through the display or by other means to ask if the operator has induced a pressure change. An audio attention alert, such as a short audible beep, may also be provided to audibly alert the operator that the processor is making a query. If the operator responds that the pressure change has been induced, the processor will indicate that no pressure change was sensed in the right pump. Such an indication may result if the conduit in which the pressure change was induced is not connected to the right pump 22 or a manual clamp on the conduit upstream from the pressure sensor is closed. As a result, the processor may display a "wrong conduit" alert indication visually on the display 54 of the infusion pump 22 and an audible alarm from the speaker of the pump. The alert indication may also be provided on the display 62 and/or speaker 58 of the programming module 60.

If the operator responds that a pressure change has not yet been induced, the processor may begin a new time period in which it waits for an induced pressure change. The new time period may be the same as the preceding time period or it may be different. In another embodiment, the processor may switch to a "suspend" mode in which it suspends further operation until the operator presses a particular key, such as the ENTER key as one of the input devices 90, at which time, the processor will once again enter a time period of the verification mode in which it monitors for an induced pressure change.

If the processor 84 detects the induced pressure change within the predetermined time period, the processor may provide a verification indication on displays 54 (FIG. 2) or 62 and then terminate the delay of operation of the flow control device 70. That is, the processor no longer inhibits pump operation but instead, allows the pump to begin pumping at the initiation of the operator. After any further programming of the pump is completed, such as by pressing the START key, the processor will control the flow control device to begin the infusion and move fluid through the fluid conduit 66 to the patient 48. Because operation of the flow control device is delayed until the processor detects the manually induced pressure change, the processor thereby verifies that the correct fluid conduit is connected to the correct flow control device prior to delivering the fluid to the patient.

Further detail on the connection verification mode of operation in accordance with an embodiment of the present invention will now be described. In reference to FIGS. 1 through 4, a nurse begins the process by hanging a bag 38 of medication from a stand, such as the roller stand 46 shown in FIG. 1, priming the conduit of a fluid administration set 30 with the fluid from the fluid supply to be infused into the patient 48. If the fluid supply has a bar code label, or other information device, containing pump operating parameters, the nurse may read it into the pump through a bar code reader, infrared transfer, or other means to automatically program the pump. The conduit is connected to the pump and if automatic programming of the pump has not occurred, the nurse may manually program the pump through the use of the control keys 56 or 64, for example.

The nurse may also use the control keys 64 on the programming module 60 to select a drug from a data base of drugs stored in a drug library 92 (FIG. 4), the drug library being stored in the memory 88 of the patient care system 20. In one embodiment, the drug library is stored in the memory of the programming module 60 (FIG. 2) and a scrolling list of drugs may be displayed on the display 62 of the programming module 60 (FIG. 2) for selection. The drug library may also include flow rates, doses, and other information that can be selected and which represents the best practices of the clinic in which the pump is located. In a further system, the programming module, infusion pump, or other processing device may contain a drug library having drug names and accepted best practices of the clinic for administration of that drug.

Before a pump is allowed to infuse a drug into a patient, the processor is also configured through programming to check the pump's programming against the drug library 92. The drug library may also include pumping limits and in one case, "soft" limits may exist. If the operator of the pump were to select a pumping parameter that is outside a "soft" limit, a "soft" alert may be provided by the processor to the operator as an indication that he or she has programmed a parameter that is outside a limit. However, a "soft" limit can be overridden by the operator and pumping may be commenced. The drug library may also include "hard" limits. If the operator of the pump were to select a pumping parameter that is outside a "hard" limit, a "hard" alert may be provided by the processor to the operator as an indication that he or she has programmed a parameter that is outside a hard limit. A "hard" limit cannot be overridden by the operator and pumping will not be permitted until the programmed parameter is changed to an acceptable level. Such a system providing limits and alerts through a drug library is available through the GUARDRAILS® system from ALARIS Medical Systems, Inc. The drug library of the patient care system may be configured to be periodically updated through the communications system using an external device such as a computer running appropriate software.

In an embodiment, the drug library 92 may also include drug entries linked to an instruction that the processor controlling a flow control device is to run the connection verification mode. In particular, selected drugs may include such an instruction in addition to dosages, and pumping parameters. This approach would automatically put the processor in the connection verification mode without further operator input. Therefore, once an operator enters a drug name that is in the library, and if that drug name includes a link to instruct the processor to run the connection verification mode, the processor will automatically begin the verification mode.

Figure 5:
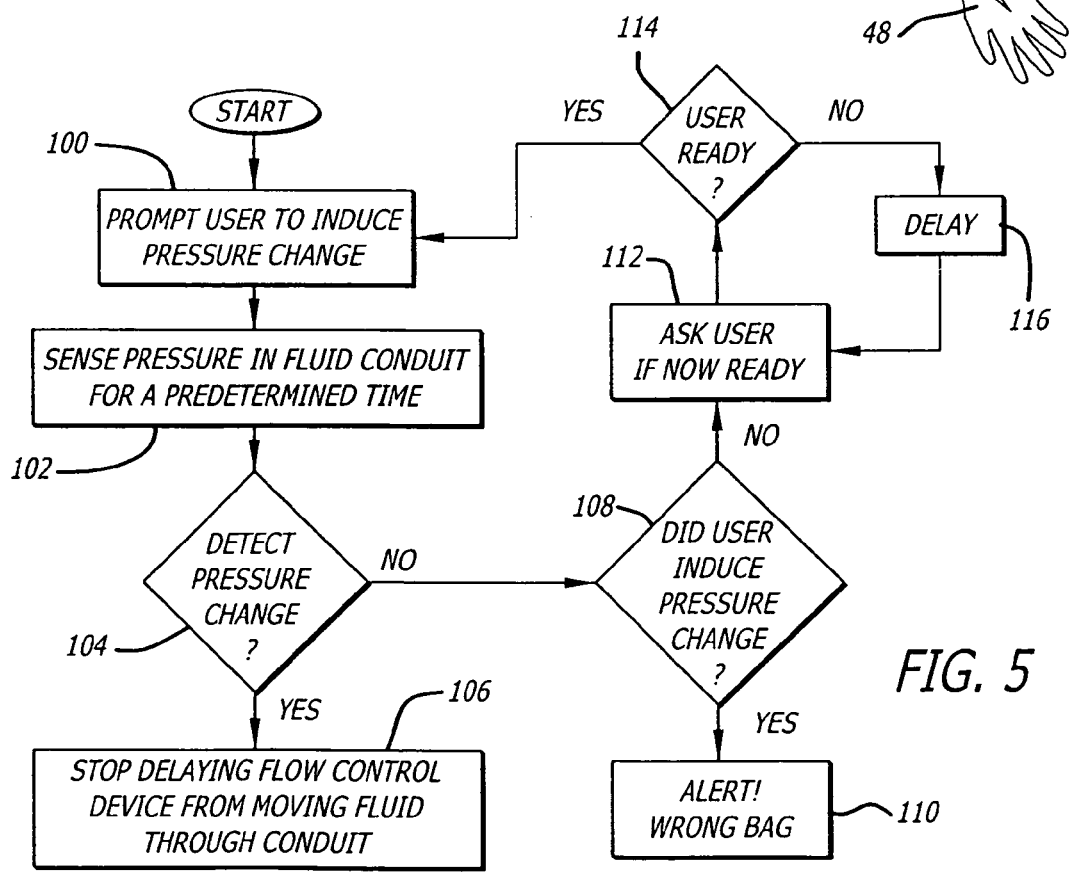
FIG. 5 is a flow chart depicting one embodiment of a method incorporating aspects of the present invention, for verifying that the correct fluid source is connected to a pump.

Turning now to FIG. 5 in which is shown an embodiment of a method in accordance with aspects of the invention, the operator is prompted to induce a pressure change in the fluid conduit, in box 100, such as by squeezing, raising, or lowering the fluid supply 38 to ensure connection of the correct fluid supply to the correct pump 22. This is done before fluid delivery begins. In box 102, the pressure in the fluid conduit is sensed by the upstream pressure sensor 80 (FIG. 4), as previously described. As indicated by box 102, in one embodiment, the pressure may be sensed for a predetermined time period. The processor 84 monitors the pressure signals received from the upstream pressure sensor 80 and delays fluid delivery until the processor detects the induced pressure change in the fluid conduit, as indicated by boxes 104 and 106.

If a pressure change is detected, box 104, the processor stops delaying the flow control device, permitting further programming to continue and pumping to commence, box 106. Optionally, an appropriate message may also be displayed on display 54 or 62 to inform the operator of the detection of the induced pressure change.

On the other hand, if the processor did not detect a pressure change in the predetermined time period, it may provide a query to the operator to ask if a pressure change was induced, box 108. If the operator responds that a pressure change was induced, the processor provides an alert, box 110, indicating that the wrong conduit or bag is connected to the pump and continues to delay fluid delivery. In the case of FIG. 5, the alarm indication given is ALERT! WRONG BAG. However, the actual visual alert notification may take different forms; FIG. 5 presents only one embodiment. For example, the notification may also say CHECK FOR CLOSED UPSTREAM CLAMP or THE SET HAS BEEN INSTALLED IN WRONG PUMP, or other. The alert indication may also be made audibly by means of a speaker. Such an alert is referred to as a "connection verification" alarm or alert herein in various places, although it is also referred to in other ways.

If the operator indicates that a pressure change was not induced, the processor will query the operator to determine if the operator is now ready to induce a pressure change, box 112. If the operator is now ready. box 114, the process repeats 100. If the operator is not ready, a delay is imposed in box 116, and the operator is then asked again if he or she is ready, box 112.

The processor further includes an override mode in which the connection verification mode can be overcome by an operator and infusion can begin immediately. The processor 84 will permit the operator of the pump 22 to override a connection alert indication and proceed with the delivery of medical fluid. Data concerning such connection verification overrides will be stored in a memory 88 for record-keeping purposes along with other infusion-related events, such as the occurrences of "soft" and "hard" alarms that occur because of programming parameters that exceed such limits. Overrides of "soft" limits and alarms could also be stored in memory.

Figure 6:
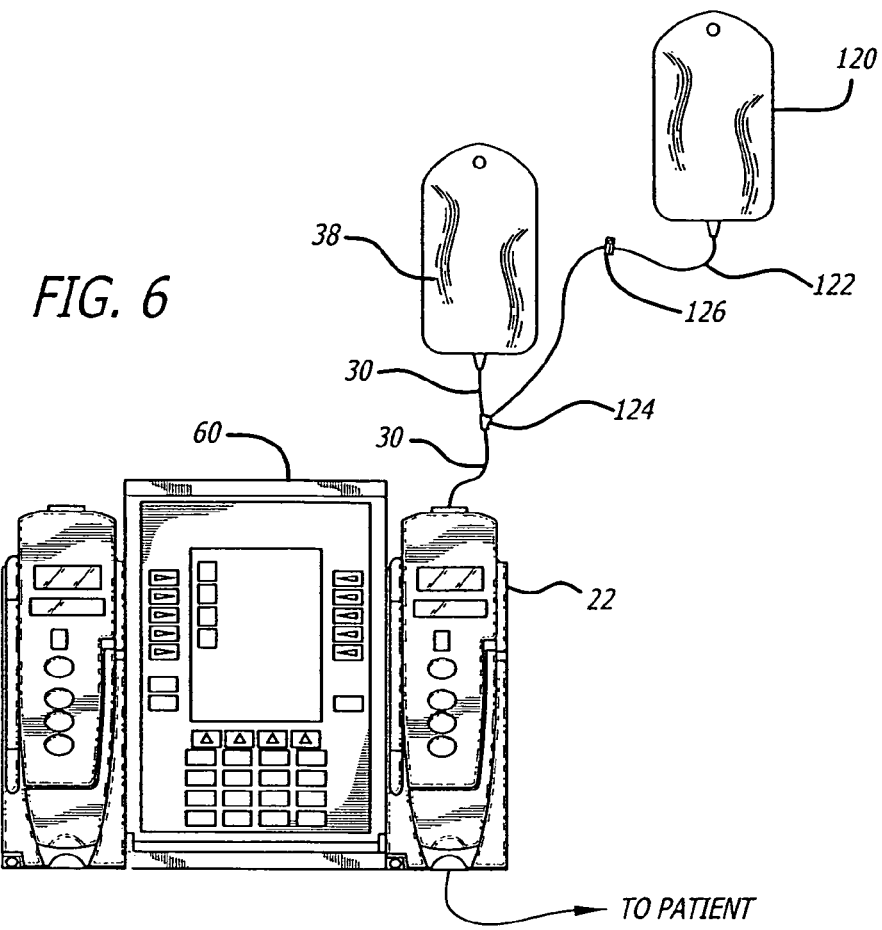
FIG. 6 is a view of the patient care system of FIG. 1 having a programming module and two infusion pumps with one of the infusion pumps having mounted to it the tube of an administration set that is connected upstream of the pump to a primary fluid supply and to a secondary fluid supply for administering a piggyback infusion.

In accordance with aspects of the present invention, a nurse can also verify the proper connection of a secondary fluid supply 120, as shown in FIG. 6, for a secondary (e.g., piggyback) infusion. In a typical secondary infusion, the nurse attaches a secondary fluid conduit 122 associated with the secondary fluid supply 120 to the primary administration set 30 of the primary fluid supply 38 by means of a Y-site port 124. The processor 84 may then verify that the secondary fluid supply has been correctly connected in the same manner as previously described with respect to primary fluid supplies. That is, the configured processor requests that a pressure change be induced in the secondary line. When the processor does not detect a pressure change in the fluid conduit after inducing a pressure change in the secondary fluid line, two types of connection errors may be indicated. First, the secondary fluid supply may be connected to the wrong pump or pump channel. Second, the connection between the pump channel and the secondary fluid supply 120 may not have been established because of failure to open a manual clamp, such as a slide clamp 126, located on the secondary fluid conduit 122. In either case, the system and method of the present invention will determine that the proper connection cannot be verified and can alert the operator to the error.

Figure 7:
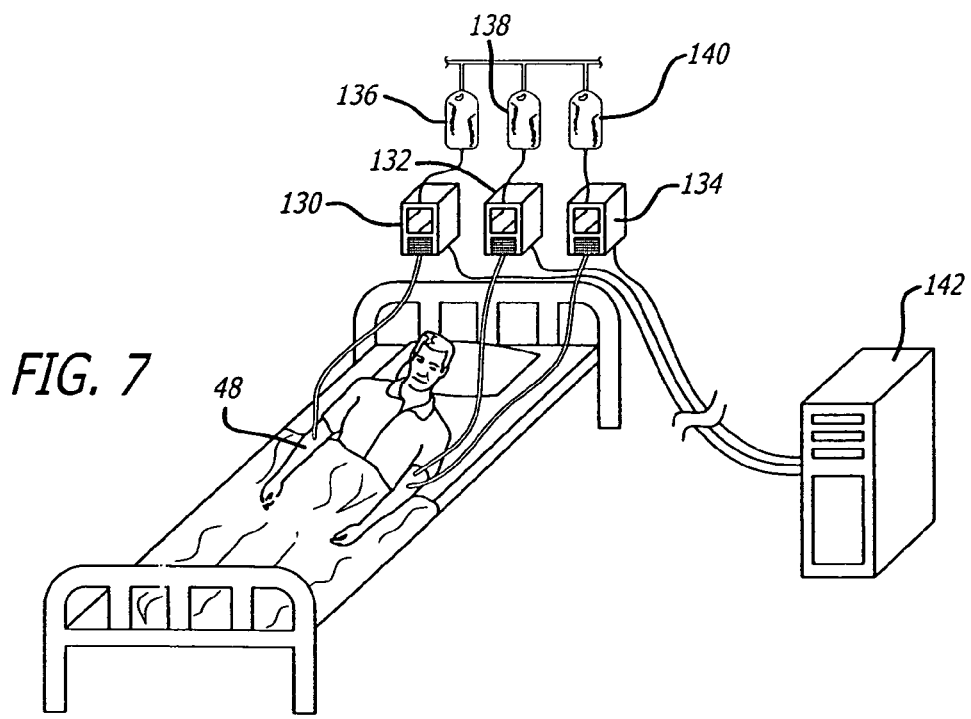
FIG. 7 presents an arrangement where a patient is receiving infusions from three separate infusion pumps but all pumps are networked by a single computer.

In FIG. 7, three separate single channel pumps 130, 132, and 134 are being used for a single patient 45. A separate fluid supply 136, 138, and 140 is designated for each pump. The pumps are all networked in this case to a common processor or server 142. Each pump may have its own connection verification system and may require that the operator induce a pressure change in each fluid supply and the pressure change be detected by that pump before infusion by the particular pump can begin. However, in such a local connection verification system approach, the pump that does not detect the induced pressure because the set has been misloaded cannot then inform the operator in which pump that fluid supply actually has been installed. This can be overcome with the network approach shown in FIG. 7. The network processor 142 is connected to all pumps 130, 132, and 134 and may monitor each pump for connection verification. In one embodiment, the network processor 142 may actually perform the connection verification for each networked pump. The upstream pressure sensor of each pump can be monitored by the network processor and when the operator is prompted to induce a pressure change in one fluid line, the network processor can monitor the upstream pressure sensors of all pumps. Thus, if the induced pressure change is not detected in the right pump, the network processor can determine which pump in fact the pressure change was detected and inform the operator. The operator will then be able to locate the conduit that is installed in the wrong pump and promptly install it in the correct pump. As mentioned above, this approach also works in the MED-LEY® system where a single programming module 60 (FIG. 2) monitors all infusion modules 22, 24, 26, and 28.

From the foregoing, it will be appreciated that the system and method in accordance with the principles of the invention provide effective means to determine that a fluid supply is correctly connected to an infusion pump in order to ensure infusion of the proper drug.

I claim:

1. A system for verifying that a particular fluid supply containing a fluid is connected to a flow control device, wherein a tube is connected to the fluid supply, the tube having an inner surface for carrying the fluid and an outer surface and the flow control device acts on a tube coupled to the fluid supply to control movement of the fluid from the fluid supply through the conduit, the system comprising:

a pressure sensor coupled to the outer surface of the tube, the pressure sensor providing pressure signals representative of pressure in the tube; and a processor having a connection verification mode in which the processor is configured to monitor the pressure signals for a predetermined time period to detect an operator-induced pressure change and to provide a verification indication when the processor receives pressure signals indicative of the operator-induced pressure change in the conduit to thereby verify that the particular fluid supply is connected to the flow control device;

wherein the processor in the connection verification mode is further configured to:

prompt the operator to confirm that a pressure change has been induced if the operator-induced pressure change is not detected within the predetermined time period.

2. The system of claim 1 wherein the processor in the connection verification mode is further configured to provide an alert indication if the operator confirms that the pressure change has been induced but the processor has not detected the operator-induced pressure change indicated by the pressure signals within the predetermined.

3. A patient care system for infusing multiple medical fluids, the patient care system comprising:

a plurality of fluid containers each adapted to hold a separate medical fluid;

a plurality of fluid conduits each in fluid communication with a separate fluid container from among the plurality of fluid containers;

a plurality of pump channels each adapted to receive and connect to a separate fluid conduit from among the plurality of fluid conduits and to operate on the received conduit to pump the fluid from the fluid container connected to the received conduit;

a plurality of pressure sensors each associated with a pump channel, each coupled to a separate fluid conduit from among the plurality of fluid conduits, and each located upstream of the associated pump channel providing the sensor signals representative of pressure in the fluid conduit with which the pressure sensor is coupled; and a processor connected to the plurality of pressure sensors and to the plurality of pump channels, the processor configured to verify that a particular fluid container from among the plurality of fluid containers is connected to a particular pump channel from among the plurality of pump channels;

wherein the processor has a connection verification mode in which the processor is configured to monitor the pressure signals for a predetermined time period to detect an operator-induced pressure change and to provide a verification indication when the processor receives pressure signals indicative of the operator-induced pressure change in a particular conduit to thereby verify that the particular fluid container is connected to the particular pump channel through the particular conduit.

4. The patient care system of claim 3 wherein the processor is further configured to delay a pump channel from moving fluid through the respective conduit until the processor receives pressure signals indicative of the operator-induced pressure change in the respective conduit.

5. The patient care system of claim 3 wherein the processor in the connection verification mode is configured to detect that the operator-induced pressure change is at any of the pump channels with which the processor is connected and indicate an identity to the operator of the pump channel at which the operator-induced pressure change was actually detected.

6. The patient care system of claim 3 wherein the processor in the connection verification mode is further configured to:

prompt an operator to induce a pressure change in the particular fluid conduit.

7. The patient care system of claim 3 wherein the processor in the connection verification mode is further configured to:
prompt the operator to confirm that a pressure change has been induced if the operator-induced pressure change is not detected within the predetermined time period.

8. The patient care system of claim 7 wherein the processor in the connection verification mode is further configured to provide an alert indication if the operator confirms that the pressure change has been induced but the processor has not detected the operator-induced pressure change indicated by the pressure signals within the predetermined time period.

9. The patient care system of claim 6 wherein the processor in the connection verification mode is configured to prompt the operator to squeeze the particular fluid supply or the conduit in fluid communication with the particular fluid supply to induce the pressure change.

10. The patient care system of claim 6 wherein the processor in the connection verification mode is configured to prompt the operator to change the height of the particular fluid supply to induce the pressure change.

11. The patient care system of claim 6 wherein the processor in the connection verification mode is configured to prompt the operator to tap the particular fluid supply or the conduit in fluid communication with the particular fluid supply to induce the pressure change.

12. The patient care system of claim 3 wherein the processor further includes an override mode, the processor being configured such that when in the override mode, the processor does not run the verification mode.

13. The patient care system of claim 3 further comprising:
a drug library in which is stored a data base of drugs, wherein the drug data base also includes instructions linked to selected drugs to instruct the processor to run the connection verification mode; and
an input device coupled to the processor by which a selection of a drug from the drug data base is made;
wherein the processor receives the drug selection from the input device, accesses the drug library, and is configured in the connection verification mode in the event that such an instruction is linked to the selected drug.

14. A method for verifying that a particular fluid supply is connected to a pump mechanism wherein the pump mechanism acts on a fluid conduit coupled to the fluid supply to control movement of fluid from the fluid supply through the fluid conduit, the method comprising:
prompting an operator to induce a pressure change in the fluid conduit;
sensing pressure in an upstream portion the fluid conduit located between the fluid supply and pump mechanism and generating pressure signals representative of the pressure in the upstream portion of the fluid conduit;
monitoring the pressure signals for a predetermined period of time;
processing the pressure signals to detect an operator-induced pressure change in the upstream portion of the fluid conduit in response to the step of prompting the operator to induce the pressure change; and
indicating a connection verification that the fluid supply is connected to the pump mechanism when the operator-induced pressure change is detected from processing the pressure signals.

15. The method of claim 14 further comprising delaying the flow control device from moving fluid through the conduit until the pressure change in the fluid conduit is detected.

16. The method of claim 14 further comprising:
detecting the operator-induced pressure change at a second flow control device; and
indicating an identity of the second flow control device.

17. The method of claim 14 further comprising:
comprising prompting the operator to confirm that a pressure change has been induced if the induced pressure change is not detected within the predetermined time period.

18. The method of claim 17 further comprising alerting the operator if the operator confirms that the pressure change has been induced but the processor has not detected a pressure change indicated by the pressure signals within the predetermined time period.

19. The method of claim 14 further comprising prompting the operator to squeeze the fluid supply or the fluid conduit to induce the pressure change in the fluid conduit.

20. The method of claim 14 further comprising prompting the operator to change the height of the fluid supply to induce the pressure change in the fluid conduit.

21. The method of claim 14 further comprising prompting the operator to tap the fluid supply or the fluid conduit to induce the pressure change in the fluid conduit.

22. The method of claim 14 further comprising selectively overriding the processing and indicating steps.

23. The method of claim 14 further comprising:
storing a drug library comprising a data base of drugs, wherein the drug data base also includes instructions linked to selected drugs to run a connection verification method; and
selecting a drug from the drug data base;
accessing the drug library and performing the prompting, sensing, processing and indicating steps in the event that such an instruction is linked to the selected drug.

24. A system for verifying that a particular fluid supply is connected to a flow control device, wherein the flow control device acts on a fluid conduit coupled to the fluid supply to control movement of the fluid from the fluid supply through the conduit, the system comprising:
a pressure sensor coupled to the fluid conduit, the pressure sensor providing pressure signals representative of pressure in the fluid conduit; and
a processor having a connection verification mode in which the processor is configured to monitor the pressure signals for a predetermined time period to detect an operator-induced pressure change, to prompt the operator to confirm that a pressure change has been induced if the operator-induced pressure change is not detected within the predetermined time period, and to provide a verification indication when the processor receives pressure signals indicative of the operator-induced pressure change in the conduit to thereby verify that the particular fluid supply is connected to the flow control device.

25. A patient care system for infusing multiple medical fluids, the patient care system comprising:
a plurality of fluid containers each adapted to hold a separate medical fluid;
a plurality of fluid conduits each in fluid communication with a separate fluid container from among the plurality of fluid containers;
a plurality of pump channels each adapted to connect to a separate fluid conduit from among the plurality of fluid conduits and to operate on the received conduit to control movement of fluid from the fluid container connected to the received conduit;

a plurality of pressure sensors each associated with a pump channel, each coupled to a separate fluid conduit from among the plurality of fluid conduits, and each providing sensor signals representative of pressure in the fluid conduit with which the pressure sensor is coupled; and a processor connected to the plurality of pressure sensors and to the plurality of pump channels, the processor configured to verify that a particular fluid container from among the plurality of fluid containers is connected to a particular pump channel from among the plurality of pump channels;

wherein the processor has a connection verification mode in which the processor is configured to monitor the pressure signals for a predetermined time period to detect an operator-induced pressure change, to prompt the operator to confirm that a pressure change has been induced if the operator-induced pressure change is not detected within the predetermined time period time, and to provide a verification indication when the processor receives pressure signals indicative of the operator-induced pressure change in a particular conduit to thereby verify that the particular fluid container is connected to the particular pump channel through the particular conduit.

26. A method for verifying that a particular fluid supply is connected to a flow control device, wherein the flow control device acts on a fluid conduit coupled to the fluid supply to control movement of fluid from the fluid supply through the fluid conduit, the fluid supply and fluid conduit forming an upstream fluid supply segment, the method comprising:

prompting an operator to induce a pressure change in the fluid conduit;

sensing pressure in the fluid conduit and generating pressure signals representative of the pressure in the fluid conduit;

monitoring the pressure signals for a predetermined period of time.

processing the pressure signals to detect an operator-induced pressure change in the fluid conduit in response to the step of prompting the operator to induce the pressure change;

alerting the operator if the operator confirms that the pressure change has been induced but the processor has not detected a pressure change indicated by the pressure signals within the predetermined time period; and indicating a connection verification that the fluid supply is connected to the flow control device when the operator-induced pressure change is detected from processing the pressure signals.

* * * * *